United States Patent
McDerment

(10) Patent No.: US 6,176,238 B1
(45) Date of Patent: Jan. 23, 2001

(54) DISPENSER FOR SUBSTANCES IN POWDER OR GRANULAR FORM

(75) Inventor: Iain McDerment, Royston (GB)

(73) Assignee: Miat S.P.A., Milan (IT)

( * ) Notice: Under 35 U.S.C. 154(b), the term of this patent shall be extended for 0 days.

(21) Appl. No.: 09/191,420

(22) Filed: Nov. 12, 1998

(30) Foreign Application Priority Data

Nov. 12, 1997 (IT) ............................................. MI970805 U

(51) Int. Cl.⁷ ....................... A61M 15/00; A61M 16/00; B05D 7/14; B65D 83/06
(52) U.S. Cl. ........................... 128/203.15; 222/153.13; 222/402.11
(58) Field of Search ......................... 128/203.12, 203.15; 604/58; 222/636, 153.01, 153.04, 153.13, 153.14, 402.11

(56) References Cited

U.S. PATENT DOCUMENTS

| | | | | |
|---|---|---|---|---|
| 2,642,063 | * | 6/1953 | Brown ............................... | 128/203.15 |
| 2,954,904 | * | 10/1960 | Potoczky .......................... | 222/153.04 |
| 3,186,605 | * | 6/1965 | Potoczky .......................... | 222/153.04 |
| 3,734,330 | * | 5/1973 | Danner et al. .......................... | 215/9 |
| 3,756,477 | * | 9/1973 | Prussin et al. .................. | 222/402.22 |
| 3,788,523 | * | 1/1974 | Thomas ................................ | 222/153 |
| 4,078,687 | * | 3/1978 | Zapp ..................................... | 215/210 |
| 4,121,741 | * | 10/1978 | Adamson ............................ | 222/181 |
| 4,809,753 | * | 3/1989 | Fink, Jr. ............................... | 141/206 |
| 4,969,584 | * | 11/1990 | Joulia ............................... | 222/402.11 |
| 5,033,463 | * | 7/1991 | Cocozza .......................... | 128/203.21 |
| 5,038,964 | * | 8/1991 | Bouix ...................................... | 222/153 |
| 5,046,493 | * | 9/1991 | Kropkowski et al. .......... | 128/203.15 |
| 5,082,148 | * | 1/1992 | Dunning ............................... | 222/162 |
| 5,205,424 | * | 4/1993 | Gasper ................................ | 215/210 |
| 5,348,199 | * | 9/1994 | Smith ............................... | 222/402.19 |
| 5,388,572 | * | 2/1995 | Mulhauser et al. ............. | 128/203.15 |
| 5,549,101 | * | 8/1996 | Trofast et al. .................. | 128/203.15 |
| 5,582,162 | * | 12/1996 | Petersson ....................... | 128/203.15 |
| 5,690,256 | * | 11/1997 | Smith ............................... | 222/402.1 |

FOREIGN PATENT DOCUMENTS 0 424 790   5/1991   (EP) .
MI96A1448   1/1998   (IT) .

* cited by examiner

Primary Examiner—John G. Weiss
Assistant Examiner—Joseph F. Weiss, Jr.
(74) Attorney, Agent, or Firm—Ladas & Parry

(57) ABSTRACT

The dispenser enables a multiplicity of doses of a substance in powder or granular form contained in a reservoir to be dispensed in succession. To form a dose a shaft must be rotated relative to a part of the dispenser, the shaft having to be substantially vertical while the dose is being formed.

Between the shaft and said part of the dispenser there is provided a joint which prevents relative rotation if the shaft is not substantially vertical, or which although allowing relative rotation enables a signal to be emitted which can be sensed by the user. In particular the dispenser can be a multi-dose inhaler for medicaments.

40 Claims, 4 Drawing Sheets

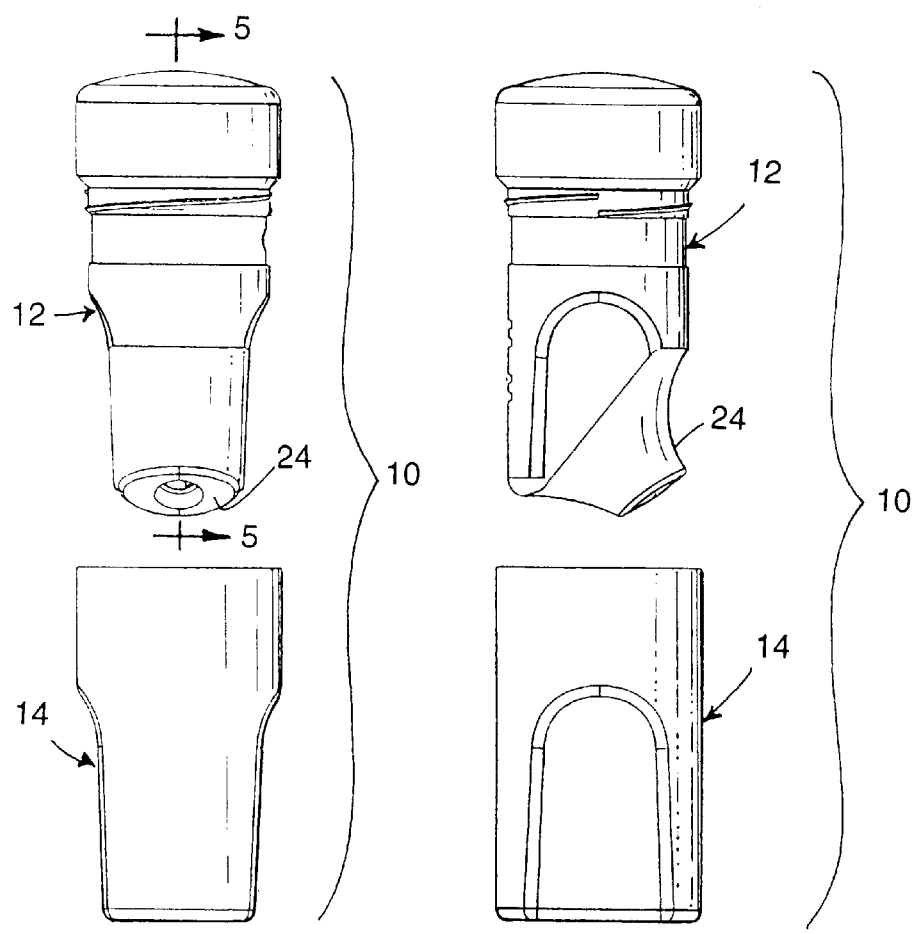
FIG. 1
FIG. 2
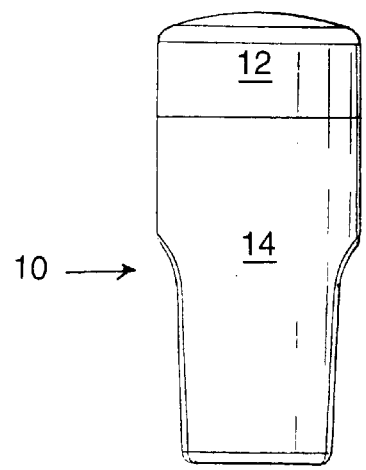
FIG. 3

DISPENSER FOR SUBSTANCES IN POWDER OR GRANULAR FORM

BACKGROUND

This invention relates to a dispenser for dispensing a multiplicity of doses of a substance in powder or granular form contained in a reservoir forming part of the dispenser, this latter being of the type in which to form a dose a shaft must be rotated relative to a part of the dispenser, the shaft having to be substantially vertical while the dose is being formed.

A dispenser of the aforesaid type is described for example in Italian patent application MI96A001448 of the present applicant. Such a dispenser falls within the scope of protection of EP-B0424970 and in addition is provided with a closure and protection adaptor which has to be removed, or opened, to enable the user to gain access to the individual dose dispensed. The presence of said adaptor is particularly useful if the dispenser is an inhaler for medicaments in powder form, and the individual dose to be administered to the patient is so small that the patient is unable to tell whether the dose has been effectively inhaled or not. In this respect, to be able to inhale the dose the patient has to remove or open the adaptor, this requiring a first part of the actual inhaler unit (ie without the adaptor) to be rotated relative to a second part, this automatically resulting in the formation of a dose of medicament withdrawn from a reservoir.

The application or, respectively, the closure of the adaptor restores the initial condition.

The accompanying FIGS. 1 to 5 illustrate, as an example of a dispenser falling within the scope of MI96A001448, a multi-dose inhaler for medicaments in powder form, provided with a removable adaptor. An English-language translation of Italian patent application no. MI96A001448 is set forth in Appendix A, which is incorporated herein by this reference. These figures basically reproduce the analogous figures of Italian patent application MI96A001448 (however retaining only the reference numerals of interest herein).

SUMMARY OF THE INVENTION

The invention includes a dispenser for dispensing a multiplicity of doses of substance in powder or granular form, said dispenser including a reservoir, a vertically disposed shaft rotatable relative to an adjacent part of the dispenser, the metering of the substance from the reservoir resulting from the rotation of the shaft about its axis, and wherein proper metering of the substance depends on the substantially vertical orientation of the shaft, wherein the dispenser includes a coupling responsive to the orientation of the shaft so as to interfere with relative rotation between the shaft and said part if the shaft does not have substantially vertical orientation.

BRIEF DESCRIPTION OF THE DRAWINGS

FIG. 1 is a front elevation of said multi-dose inhaler provided with an adaptor, this latter being shown separated from the actual inhaler unit;

FIG. 2 is a side elevation thereof;

FIG. 3 is a front elevation thereof but with the adaptor applied;

DETAILED DESCRIPTION

Figure 4:
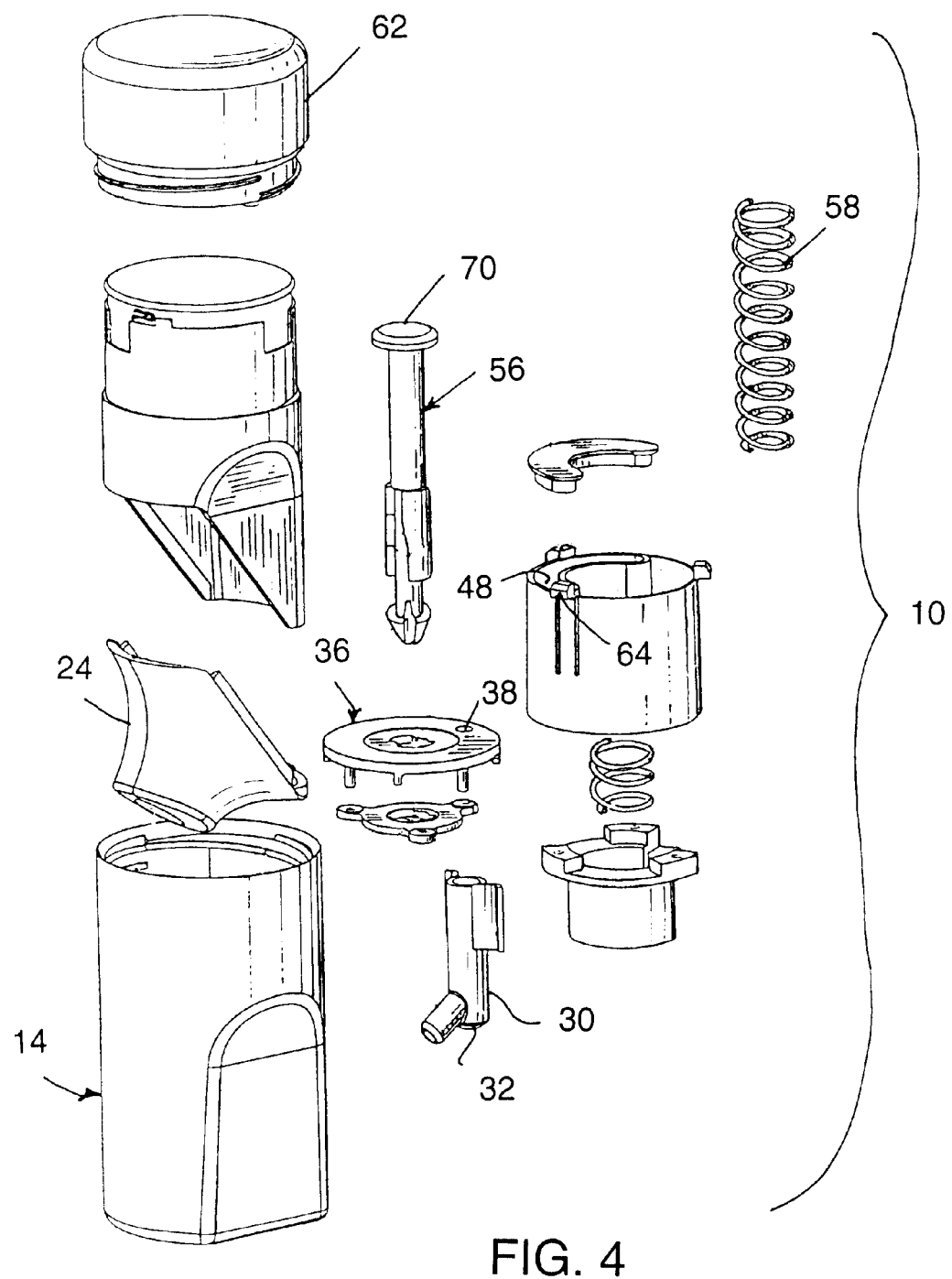
FIG. 4 is an exploded perspective view thereof.
Figure 5:
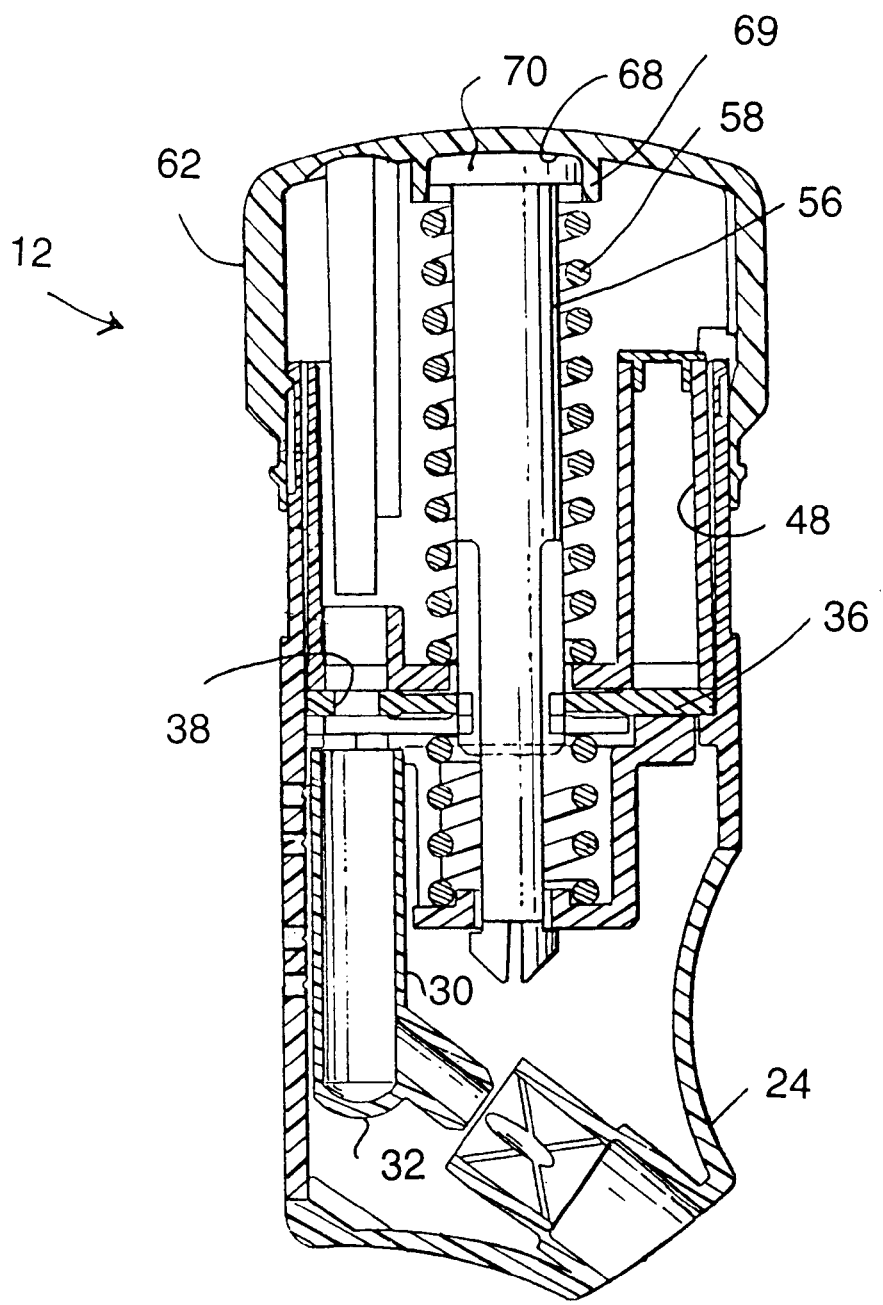
FIG. 5 is an enlarged vertical section therethrough without the adaptor, taken on the line 5—5 of FIG. 1.

As can be seen from these figures, the multi-dose inhaler 10 for medicaments in powder form, provided with a removable adaptor 14, comprises a shaft 56 which can rotate (together with the adaptor 14 while this latter is being removed by unscrewing it, or reapplied by screwing it on) relative to the cover 62. In this respect, the upper end or head 70 of the shaft 56 (FIG. 5) is received in a recess 68 which does not prevent relative rotation between the cover 62 and the shaft 56. As already stated, removing the adaptor 14 from the actual inhaler unit 12 causes a withdrawal and metering unit (which will not be described in detail herein as it is outside the stated objects) to operate in order to withdraw from the reservoir 48 (FIGS. 4 and 5) a dose of medicament in powder form and bring it into a position in which, by pressing the cover 62 (which can be moved vertically in the two directions in the manner of a pushbutton by virtue of the helical spring 58) with the fingers, the prepared dose is made to fall into the conduit 30 and deposit on its concave base, from whence it can be removed as a result of the sucking action exerted by the patient through the mouthpiece 24.

With reference to the inhaler 10, it has been found that if the inhaler 10 is not maintained substantially vertical while the adaptor 14 is being removed, and if the quantity of powder medicament in the reservoir 48 is small (the powder behaving practically as a liquid), it can happen that the powder does not completely cover that part of the disc 36 (FIGS. 4 and 5) which closes the base of the reservoir 48, with the risk that the metering hole 38 present in the disc 36 is not completely filled with powder. It follows that the medicament dose formed could be less than that prescribed or in any event not homogeneous. Precisely to avoid this problem, the operating instructions accompanying said inhaler must tell the patient to maintain the inhaler substantially vertical while the adaptor is being removed. There is however the risk that some patients, although having read said instructions, forget to maintain the inhaler vertical, with the result that only small or in any event non-constant doses of medicament are administered to the patient because of the inclination of the inhaler.

The object of the present invention is to overcome said drawback of known dispensers of the aforesaid type.

This object is attained by the dispenser of the present invention, characterized in that between said shaft and an adjacent part of the actual dispensing unit relative to which the shaft rotates while the adaptor is being removed or opened (i.e., while the dose is being formed) there is provided a coupling (or joint) which prevents the shaft from rotating relative to said part if the shaft is not substantially vertical, or a coupling (or joint) which although allowing relative rotation causes (or enables) a signal to be emitted which can be sensed by the user.

In this manner the administration of reduced or unsuitable doses can be prevented. In this respect the user either cannot remove the adaptor or receives a signal (for example the user is warned by a series of clicks that the dose formed may not be as prescribed). The user then has merely to repeat the operation while maintaining the dispenser upright, to complete the prescribed dose for dispensing.

The aforesaid coupling or joint can for example comprise a recess provided in one end of the shaft and formed from a series of angularly equidistant radial cavities having a common central portion, the depth of this recess, with respect to the axis of the shafts, decreasing in moving radially outwardly from the centre of the recess to its periphery, a similar recess of identical orientation being provided, coaxially facing the first, in said adjacent part of the actual dispensing unit, between the two recesses there being inserted a ball of diameter not exceeding the maximum depth of each of the two recesses, the sum of the minimum depth of the two recesses not being less than the ball diameter, the minimum depth of each recess being substantially less that the ball diameter.

Figure 7:
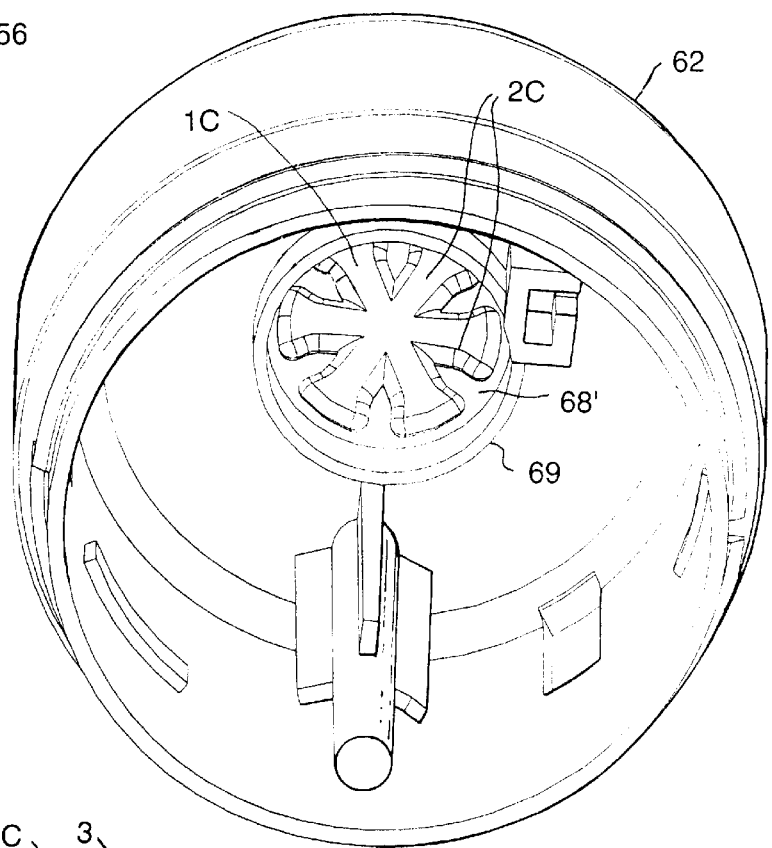
FIG. 7 is a perspective view of said cover taken from below.
Figure 8:
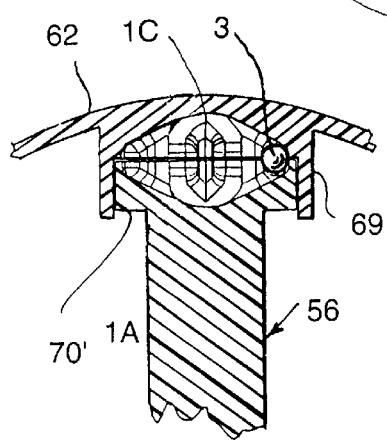
FIG. 8 is a longitudinal section taken along the axis of the shaft and cover, showing the joint between these latter, the inhaler being inclined to the vertical.

The invention will be more apparent from the following description of a multi-dose inhaler according to the invention. This description makes reference to the further accompanying FIGS. 6–8.

Figure 6:
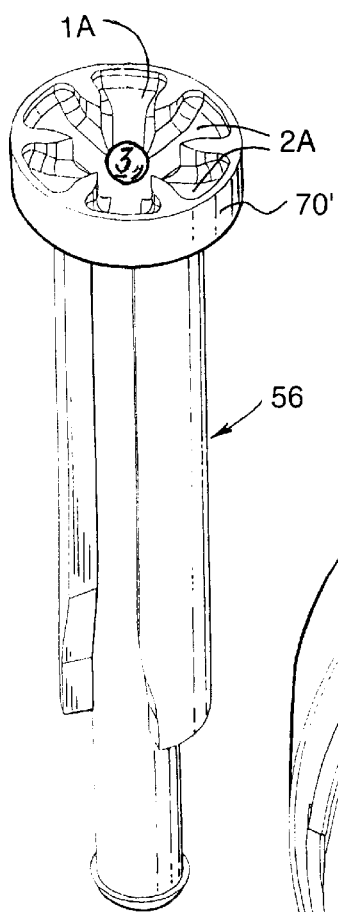
FIG. 6 is a perspective view of said shaft taken towards its head.

As can be seen from FIG. 6, the head 70' of the shaft 56 comprises a recess indicated overall by 1A (the letter A indicating that the relative reference numeral refers to the shaft). The recess 1A is composed of six angularly equidistant grooves 2A extending radially from a common central region. The overall shape of the recess 1A is similar to that of a daisy. The ribs 2A have a depth which gradually decreases from their common region to the periphery.

Within the cover 62 (FIG. 7) and bounded by a circular flange (or rib) 69 there is provided a circular cavity 68' the base of which there is a recess 1C (the letter C indicating that the relative reference numeral refers to elements of the cover) identical to the recess 1A of the shaft 56.

When the inhaler is assembled (FIG. 5) the cover must be positioned such that the two daisy recesses 1A and 1C coincide in a matching orientation. Between the two recesses there is inserted a ball 3 (preferably of stainless steel), the diameter of which must not exceed the maximum depth of each recess 1A. As is clear from the aforegoing, when the inhaler 10 is maintained vertical (so that the shaft 56 is also vertical) the ball 3 is in the position shown in FIG. 6 and does not project from the head 70' of the shaft 56, so that the shaft 56 and cover 62 can be rotated relative to each other.

If instead the inhaler 10 is held inclined (so that the ball 3 is located in the position shown in FIG. 8), when the patient attempts to remove the adaptor 14 (which requires relative rotation between the shaft 56 and cover 62) this rotation cannot proceed because of the interference of the ball, provided that the material of construction of the constituent parts of the joint is sufficiently rigid and that these parts are sufficiently robust. Consequently if the patient wishes to remove the adaptor, he is compelled to maintain the inhaler vertical.

If however the material is sufficiently elastic, rotation can take place by forcing, but in this case producing a series of clicks (with consequent noise) which warn the patient that the inhaler has not been maintained vertical, so that the dose formed by removal of the adaptor may be not that prescribed but less. In this case the patient can easily remedy the situation by simply repeating the operation, ie by reapplying the adaptor 14 and then again removing it, while maintaining the inhaler vertical.

If required, instead of said series of clicks or in addition thereto, a series of light signals could be produced, created for example by an LED powered by electric current produced piezoelectrically.

It should be noted that if the mouthpiece 24 and tube 30 are removed from the inhaler 10 or if the tube is upperly open, the inhaler becomes a normal dispenser for successively dispensed doses of any powder or granular substance (for example salt, pepper in powder form or vegetable spices for use in cookery).

The invention illustratively disclosed herein suitably may be practiced in the absence of any element which is not specifically disclosed herein.

The following claims are entitled to the broadest possible scope consistent with this application and are not necessarily limited to the embodiments illustrated in the figures.

What is claimed is:

1. A dispenser for dispensing a multiplicity of doses of a substance in a powder or granular form, said dispenser comprising:

a reservoir for holding the substance; and a shaft having an axis and an orientation, wherein the shaft is rotatable on the axis relative to an adjacent part of the dispenser;

wherein metering of the substance from the reservoir results from rotation of the shaft about the axis; wherein the metering of the substance depends on a substantially vertical orientation of the shaft; and wherein the dispenser includes a coupling responsive to the orientation of the shaft so as to interfere with the rotation of the shaft relative to said part if the shaft does not have the substantially vertical orientation.

2. A dispenser as claimed in claim 1, wherein the dispenser includes an adaptor, wherein the adaptor has to be removed or opened to enable a user to gain access to a dispensed dose.

3. A dispenser as claimed in claim 1, wherein the coupling comprises:

a first recess provided at a first end of the shaft and formed from a first series of radial cavities having a common first central portion; wherein the first recess has a depth that decreases from the first central portion to a first peripheral portion of the first recess; and wherein the first recess has a first minimum depth;

a second recess in said adjacent part and formed from a second series of radial cavities having a common second central portion; wherein the second recess has a depth that decreases from the second central portion to a second peripheral portion of the second recess; wherein the second recess has a second minimum depth; wherein the second recess faces and is aligned with the first recess; wherein the first recess and the second recess form a combined recess having a combined depth that decreases from a center portion of the combined recess to a periphery of the combined recess; wherein the combined recess has a combined maximum depth and a combined minimum depth; wherein said part is adjacent to the first end of the shaft; and a ball positioned between the first recess and the second recess; wherein the ball has a diameter that is less than the combined maximum depth of the combined recess; wherein the diameter of the ball is less than the combined minimum depth of the combined recess; wherein the first minimum depth of the first recess is less than the diameter of the ball; and wherein the second minimum depth of the second recess is less than the diameter of the ball.

4. A dispenser as claimed in claim 3, wherein the first recess is formed of a material that is elastically deformable, wherein the second recess is formed of a material that is elastically deformable, wherein the ball is formed of a substantially rigid material, wherein the shaft can rotate relative to said part when the shaft does not have the substantially vertical orientation, and wherein the dispenser produces a series of clicks noticeable to a user when the shaft is rotated relative to said part and the shaft does not have the substantially vertical orientation.

5. A dispenser as claimed in claim 3, wherein the first recess is formed of a substantially rigid material, wherein the second recess is formed of a substantially rigid material, wherein the ball is formed of a substantially rigid material, and wherein the shaft is prevented from rotating relative to said part when the shaft does not have the substantially vertical orientation.

6. A dispenser as claimed in claim 1, wherein the dispenser emits a signal if the shaft does not have a substantially vertical orientation.

7. A dispenser as claimed in claim 6, wherein the signal comprises a light signal.

8. A dispenser as claimed in claim 6, wherein the signal comprises an acoustic signal.

9. A dispenser as claimed in claim 1, wherein the dispenser is a multi-dose inhaler for a medicament.

10. A dispenser as claimed in claim 1, wherein said part is a cover for the dispenser.

11. A dispenser according to claim 1, wherein the coupling prevents rotation of the shaft relative to said part when the shaft does not have the substantially vertical orientation.

12. A dispenser according to claim 1, wherein the dispenser includes a removable adaptor, wherein removing the adaptor from the dispenser causes the shaft to rotate and results in the metering of the substance.

13. A dispenser as claimed in claim 1, wherein the coupling comprises:
   a first recess provided at a first end of the shaft;
   a second recess in said adjacent part, wherein the second recess faces and is aligned with the first recess, wherein the first recess and the second recess form a combined recess having a combined depth that decreases from a combined maximum depth to a combined minimum depth, wherein said part is adjacent to the first end of the shaft; and
   a ball positioned within the combined recess, wherein the ball has a diameter that is less than the combined maximum depth of the combined recess.

14. A dispenser as claimed in claim 13, wherein the diameter of the ball is less than the combined minimum depth of the combined recess.

15. A dispenser as claimed in claim 14, wherein the first recess has a first minimum depth; and wherein the first minimum depth of the first recess is less than the diameter of the ball.

16. A dispenser as claimed in claim 15, wherein the second recess has a second minimum depth; and wherein the second minimum depth of the second recess is less than the diameter of the ball.

17. A dispenser as claimed in claim 13, wherein the first recess has a first minimum depth; and wherein the first minimum depth of the first recess is less than the diameter of the ball.

18. A dispenser for dispensing a multiplicity of doses of a substance in a powder or granular form, said dispenser comprising:
   a reservoir for holding the substance; and
   a shaft having an axis and an orientation, wherein the shaft is rotatable on the axis relative to an adjacent part of the dispenser;
   wherein metering of the substance from the reservoir results from rotation of the shaft about the axis; wherein the metering of the substance depends on a substantially vertical orientation of the shaft; wherein the dispenser includes a coupling responsive to the orientation of the shaft so as to cause a signal to be emitted if the shaft does not have the substantially vertical orientation; and wherein the signal can be sensed by a user.

19. A dispenser as claimed in claim 18, wherein the coupling comprises:
   a first recess provided at a first end of the shaft and formed from a first series of radial cavities having a common first central portion; wherein the first recess has a depth that decreases from the first central portion to a first peripheral portion of the first recess; and wherein the first recess has a first minimum depth;
   a second recess in said adjacent part and formed from a second series of radial cavities having a common second central portion; wherein the second recess has a death that decreases from the second central portion to a second peripheral portion of the second recess; wherein the second recess has a second minimum depth; wherein the second recess faces and is aligned with the first recess; wherein the first recess and the second recess form a combined recess having a combined death that decreases from a center portion of the combined recess to a periphery of the combined recess; wherein the combined recess has a combined maximum death and a combined minimum depth; wherein said part is adjacent to the first end of the shaft; and
   a ball positioned between the first recess and the second recess; wherein the ball has a diameter that is less than the combined maximum depth of the combined recess; wherein the diameter of the ball is less than the combined minimum depth of the combined recess; wherein the first minimum depth of the first recess is less than the diameter of the ball; and wherein the second minimum depth of the second recess is less than the diameter of the ball.

20. A dispenser as claimed in claim 19, wherein the first recess is formed of a material that is elastically deformable, wherein the second recess is formed of a material that is elastically deformable, wherein the ball is formed of a substantially rigid material, wherein the shaft can rotate relative to said part when the shaft does not have the substantially vertical orientation, wherein the signal is a series of clicks, and wherein the dispenser produces the series of clicks when the shaft is rotated relative to said part and the shaft does not have the substantially vertical orientation.

21. A dispenser as claimed in claim 19, wherein the first recess is formed of a substantially rigid material, wherein the second recess is formed of a substantially rigid material, wherein the ball is formed of a substantially rigid material, and wherein the shaft is prevented from rotating relative to said part if the shaft does not have the substantially vertical orientation.

22. A dispenser as claimed in claim 18, wherein the dispenser includes an adaptor, wherein the adaptor has to be removed or opened to enable a user to gain access to a dispensed dose.

23. A dispenser as claimed in claim 18, wherein the signal comprises a light signal.

24. A dispenser as claimed in claim 18, wherein the signal comprises an acoustic signal.

25. A dispenser as claimed in claim 18, wherein the dispenser is a multi-dose inhaler for a medicament.

26. A dispenser as claimed in claim 18, wherein said part is a cover for the dispenser.

27. A dispenser according to claim 18, wherein the coupling prevents rotation of the shaft relative to said part when the shaft does not have the substantially vertical orientation.

28. A dispenser according to claim 18, wherein the dispenser includes a removable adaptor, wherein removing the adaptor from the dispenser causes the shaft to rotate and results in the metering of the substance.

29. A dispenser for dispensing a multiplicity of doses of a substance in a powder or granular form, the dispenser comprising:

a reservoir for holding the substance: and a shaft;

wherein, in order to form a dose, the shaft must be rotated relative to a part of the dispenser; wherein the dispenser includes: (1) a first joint that prevents rotation of the shaft relative to said part if the shaft is not substantially vertical, or (2) a second joint that enables a signal to be emitted if the shaft is not substantially vertical, wherein the signal can be sensed by a user.

30. A dispenser as claimed in claim 29, wherein the dispenser includes an adaptor, wherein the adaptor has to be removed or opened to enable a user to gain access to a dispensed dose.

31. A dispenser as claimed in claim 29, wherein the signal comprises a light signal.

32. A dispenser as claimed in claim 29, wherein the signal comprises an acoustic signal.

33. A dispenser as claimed in claim 29, wherein the first joint or the second joint comprises:

a first recess provided at a first end of the shaft, wherein the first recess has a first minimum depth;

a second recess in said part, wherein the second recess has a second minimum depth, wherein the second recess faces and is aligned with the first recess, wherein the first recess and the second recess form a combined recess having a combined depth that decreases from a combined maximum depth to a combined minimum depth, wherein said part is adjacent to the first end of the shaft; and a ball positioned within the combined recess, wherein the ball has a diameter that is less than the combined maximum depth of the combined recess, wherein the diameter of the ball is less than the combined minimum depth of the combined recess, and wherein the first minimum depth of the first recess is less than the diameter of the ball.

34. A dispenser as claimed in claim 33, wherein the first recess is formed of a material that is elastically deformable, wherein the second recess is formed of a material that is elastically deformable, wherein the ball is formed of a substantially rigid material, wherein the shaft can rotate relative to said part when the shaft is not substantially vertical, wherein the signal comprises a series of clicks, and wherein the dispenser produces the series of clicks when the shaft is rotated relative to said part and the shaft is not substantially vertical.

35. A dispenser as claimed in claim 33, wherein the first recess is formed of a substantially rigid material, wherein the second recess is formed of a substantially rigid material, wherein the ball is formed of a substantially rigid material, and wherein the shaft is prevented from rotating relative to said part if the shaft is not substantially vertical.

36. A dispenser as claimed in claim 29, wherein the dispenser is a multi-dose inhaler for medicaments.

37. A dispenser as claimed in claim 29, wherein said part is a cover for the dispenser.

38. A dispenser as claimed in claim 29, wherein the first joint prevents rotation of the shaft relative to said part when the shaft is not substantially vertical.

39. A dispenser as claimed in claim 29, wherein the dispenser includes a removable adaptor, wherein removing the adaptor from the dispenser causes the shaft to rotate and results in formation of the dose of the substance.

40. A dispenser as claimed in claim 29, wherein the second joint allows the shaft to rotate relative to said part when the shaft is not substantially vertical.

* * * * *

UNITED STATES PATENT AND TRADEMARK OFFICE
CERTIFICATE OF CORRECTION

PATENT NO.    : 6,176,238 B1
DATED         : January 23, 2001
INVENTOR(S)   : Iain McDerment It is certified that error appears in the above-identified patent and that said Letters Patent is hereby corrected as shown below:

Title page,
Item [56], U.S. PATENT DOCUMENTS, insert:
-- 3,565,070    2/1971   Hanson et al. --
FOREIGN PATENT DOCUMENTS, insert:
-- 0 387 222        9/1990       EPO
WO 93/21980  11/1993
WO 96/16687  6/1996
WO 95/07724  3/1995
WO 95/26212  10/1995 --

Signed and Sealed this

Fifth Day of August, 2003

JAMES E. ROGAN
*Director of the United States Patent and Trademark Office*